(12) United States Patent
Beswick et al.

(10) Patent No.: US 6,495,606 B1
(45) Date of Patent: *Dec. 17, 2002

(54) NITRIC OXIDE SYNTHASE INHIBITORS

(75) Inventors: Paul John Beswick, Hitchin (GB); Savvas Kleanthous, London (GB); Robert John Young, Bedford (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/994,969

(22) Filed: Nov. 26, 2001

Related U.S. Application Data

(63) Continuation of application No. 09/701,473, filed as application No. PCT/EP99/03583 on May 27, 1999, now Pat. No. 6,355,689.

(30) Foreign Application Priority Data

May 30, 1998 (GB) .............................................. 9811599

(51) Int. Cl.[7] .................. A61K 31/13; A61K 31/195; C07C 61/04; C07C 321/00; C07C 323/00
(52) U.S. Cl. .................. 514/665; 514/531; 514/562; 562/506; 562/557
(58) Field of Search ................. 514/631, 665, 514/562; 562/506, 557

(56) References Cited

U.S. PATENT DOCUMENTS

| | | |
|---|---|---|
| 2,049,582 A | 8/1936 | Ziegler et al. |
| 4,085,217 A | 4/1978 | Kalopissis |
| 4,512,979 A | 4/1985 | Patchett et al. |
| 4,594,341 A | 6/1986 | Cheung et al. |
| 5,028,627 A | 7/1991 | Kilbourn et al. |
| 5,081,148 A | 1/1992 | Braquet et al. |
| 5,364,881 A | 11/1994 | Griffith et al. |
| 5,453,441 A | 9/1995 | Griffith |
| 5,585,402 A | 12/1996 | Moncada et al. |
| 5,863,931 A | 1/1999 | Beams et al. |
| 5,889,056 A | 3/1999 | Hodson et al. |

FOREIGN PATENT DOCUMENTS

| | | |
|---|---|---|
| DE | 830640 | 2/1952 |
| DE | 4310202 A1 | 10/1993 |
| EP | 068173 | 1/1983 |
| EP | 0 097031 A2 | 12/1983 |
| EP | 0200051 | 12/1986 |
| EP | 0446699 A1 | 9/1991 |
| FR | 2727111 | 5/1996 |
| GB | 2240041 A | 7/1991 |
| WO | WO 9104024 | 4/1991 |
| WO | WO 9313055 | 7/1993 |
| WO | WO 9534534 | 12/1995 |
| WO | WO 9830537 | 7/1998 |

OTHER PUBLICATIONS

Elmore, D. et al., Biochem.J., 102:728 (1967).
Houben–Weyl, Methoden de Organischen Chemie, Georg Thieme Veriag, NY (1985), pp. 931.
Larsson, U. et al., Acta Chem Scand 48 (6):517 (1994).
Plapp, B. et al., Analytical Biochemistry, 62:291 (1974).
Proudfoot, A. et al., J. Biol. Chem., 264 (15):8764 (1989).
Rees, D. et al., Br. J. Pharmacol., 101:746 (1990).
Tanaka, H. et al., J. Biol. Chem., 249 (16):5285 (1974).
Rinali, A. et al., "On the Synthesis of S–beta–aminomethyl–homocysteine", Italian Journal of Biochemistry, vol. 20, No. 1–2, pp. 1–5, Rome, Italy, 1971.
Hope, D.B. et al., "Synthesis of Some Dibasic Sulphur–containing Amino–acids Related to L–lysine", Journal of the Chemical Society, Section C: Organic Chemistry, No. 12, pp. 1098–1101, Letchworth, GB, 1966.

*Primary Examiner*—Mukund J. Shah
*Assistant Examiner*—Zachary C. Tucker
(74) *Attorney, Agent, or Firm*—Lorie Ann Morgan

(57) ABSTRACT

The present invention relates to novel amidino compounds of formula (I),

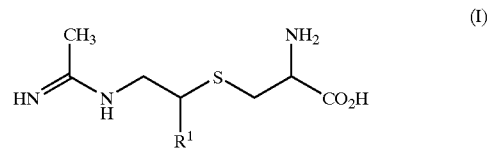

or a salt, solvate, or physiologically functional derivative thereof;

wherein $R^1$ is selected from $C_{1-4}$ alkyl, $C_{3-4}$ cycloalkyl, $C_{1-4}$ hydroxyalkyl, and $C_{1-4}$ haloalkyl; to a process for their manufacture, to pharmaceutical compositions containing them, and to their use in therapy, in particular their use as selective inhibitors of inducible nitric oxide synthase.

12 Claims, No Drawings

NITRIC OXIDE SYNTHASE INHIBITORS

CROSS REFERENCES TO RELATED APPLICATIONS

This Application is a continuation of U.S. patent application Ser. No. 09/701,473, filed Nov. 29, 2000, now U.S. Pat. No. 6,355,689, granted Mar. 12, 2002, which application was filed pursuant to 35 U.S.C. §371 as a United States National Phase Application of International Application No. PCT/EP99/03583, filed May 27, 1999, which claims priority to Great Britain Priority Patent Application Serial No. 9811599.1, filed May 30, 1998.

The present invention relates to novel amidino compounds, to a process for their manufacture, to pharmaceutical compositions containing them, and to their use in therapy, in particular their use as selective inhibitors of inducible nitric oxide synthase.

Nitric oxide is the endogenous stimulator of the soluble guanylate cyclase enzyme and is involved in a number of biological actions. Excess nitric oxide production is also thought to be involved in a number of conditions, including septic shock and many inflammatory diseases. The biochemical synthesis of nitric oxide from L-arginine is catalysed by the enzyme NO synthase. Many inhibitors of NO synthase have been described and proposed for therapeutic use.

More recently, it has been an object in this field to provide NO synthase inhibitors displaying selectivity for inducible NO synthase (iNOS) over endothelial NO synthase (eNOS) and/or neuronal NO synthase (nNOS).

Thus WO93/13055 describes selective NO synthase inhibitors of formula

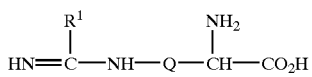

and salts, and pharmaceutically acceptable esters and amides thereof, in which:

$R_1$ is a $C_{1-6}$ straight or branched chain alkyl group, a $C_{2-6}$ alkenyl group, a $C_{2-6}$ alkynyl group, a $C_{3-6}$ cycloalkyl group or a $C_{3-6}$ cycloalkyl$C_{1-6}$ alkyl group;

Q is an alkylene, alkenylene or alkynylene group having 3 to 6 carbon atoms and which may optionally be substituted by one or more $C_{1-3}$ alkyl groups;

a group of formula —$(CH_2)_pX(CH_2)_q$— where p is 2 or 3, q is 1 or 2 and X is $S(O)_x$ where x is 0, 1 or 2, O or $NR^2$ where $R^2$ is H or $C_{1-6}$ alkyl; or a group of formula —$(CH_2)_rA(CH_2)_s$— where r is 0, 1 or 2, s is 0, 1 or 2 and A is a 3 to 6 membered carbocyclic or heterocyclic ring which may optionally be substituted by one or more suitable substituents such as $C_{1-6}$ alkyl, $C_{1-6}$ alkoxy, hydroxy, halo, nitro, cyano, trifluoro$C_{1-6}$ alkyl, amino $C_{1-6}$ alkylamino or di$C_{1-6}$ alkylamino.

The co-pending International application WO 98/30537 also describes certain amidino compounds which are selective inhibitors of inducible nitric oxide synthase.

We have now found a novel class of compounds which as well as being selective iNOS inhibitors, display advantages including that they have a relatively long half-life, are orally bioavailable when administered in vivo, and may be prepared from relatively cheap starting materials.

Therefore, according to the present invention there is provided a compound of formula (I)

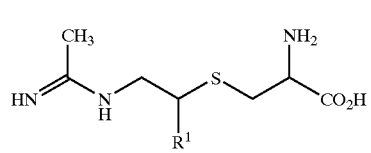

or a salt, solvate, or physiologically functional derivative thereof;

wherein $R^1$ is selected from $C_{1-4}$ alkyl, $C_{3-4}$ cycloalkyl, $C_{1-4}$ hydroxyalkyl, and $C_{1-4}$ haloalkyl.

In formula (I), $R^1$ is preferably $C_{1-4}$ alkyl, most preferably, methyl.

The compounds of formula (I) include two chiral centres i.e. the carbon which bears the $R^1$ substituent and the asymmetric centre in the amino acid group. It is intended that formula (I) includes all optical isomers either in substantially pure form or admixed in any proportions. In a preferred aspect, the amino acid group is in the natural L configuration. In a further preferred aspect the carbon bearing the group $R^1$ is in the R configuration. In the most preferred aspect, the amino acid is in the natural L configuration and the carbon bearing the group $R^1$ is in the R configuration. Throughout this specification, where the stereochemistry of two chiral centres within a molecule are given, the first configuration refers to the amino acid α carbon and the second refers to the carbon bearing the $R^1$ substituent, for example, stereochemistry designated (R,S) means (R)-stereochemistry at the amino acid a carbon, and (S)-stereochemistry at the carbon bearing the $R^1$ substituent.

Thus, in a further aspect, the present invention provides a compound selected from:

S-[(R)-2-(1-iminoethylamino)propyl]-L-cysteine;
S-[(S)-2-(1-iminoethylamino)propyl]-L-cysteine;
S-[(R/S)-2-(1-iminoethylamino)propyl]-L-cysteine;
S-[(R)-2-(1-iminoethylamino)propyl]D-cysteine;
S-[(S)-2-(1-iminoethylamino)propyl]-D-cysteine;
S-[(R/S)-2-(1-iminoethylamino)propyl]-D-cysteine;
S-[(R/S)-2-(1-iminoethylamino)butyl]-L-cysteine;
S-[(R/S)-2-(1-iminoethylamino,2-cyclopropyl)ethyl]-L-cysteine; and
S-[(R/S)-2-(1-iminoethylamino,3-hydroxy)propyl]-L-cysteine.

and salts, solvates, and physiologically functional derivatives thereof.

In a preferred aspect, the present invention provides S-[(R)-2-(1-iminoethylamino)propyl]-L-cysteine or a salt, solvate, or physiologically functional derivative thereof. In a particularly preferred aspect, the present invention provides S-[(R)-2-(1-iminoethylamino)propyl]-L-cysteine or a salt thereof.

It is to be understood that the present invention covers all combinations of particular and preferred groups described herein.

Salts and solvates of compounds of formula (I) which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of formula (I) and their pharmaceutically acceptable salts, solvates, and physiologically functional derivatives.

By the term "physiologically functional derivative" is meant a chemical derivative of a compound of formula (I)

having the same physiological function as the free compound of formula (I), for example, by being convertible in the body thereto. According to the present invention, examples of physiologically functional derivatives include esters, amides, and carbamates; preferably esters and amides.

Suitable salts according to the invention include those formed with both organic and inorganic acids or bases. Pharmaceutically acceptable acid addition salts include those formed from hydrochloric, hydrobromic, sulphuric, citric, tartaric, phosphoric, lactic, pyruvic, acetic, trifluoroacetic, succinic, oxalic, fumaric, maleic, oxaloacetic, methanesulphonic, ethanesulphorlic, p-toluenesulphonic, benzenesulphonic, and isethionic acids. Pharmaceutically acceptable base salts include ammonium salts, alkali metal salts such as those of sodium and potassium, alkaline earth metal salts such as those of calcium and magnesium and salts with organic bases such as dicyclohexyl amine and N-methyl-D-glucamine.

Pharmaceutically acceptable esters and amides of the compounds of formula (I) may have the acid group converted to a $C_{1-6}$alkyl, aryl, aryl $C_{1-6}$ alkyl, or amino acid ester or amide. Pharmaceutically acceptable amides and carbamates of the compounds of formula (I) may have an amino group converted to a $C_{1-6}$alkyl, aryl, aryl $C_{1-6}$ alkyl, or amino acid amide or carbamate.

As mentioned above, the compounds of formula (I) are inhibitors of NO synthase as demonstrated in the NOS inhibition assays below.

Therefore, compounds of formula (I) and their pharmaceutically acceptable salts, solvates, and physiologically functional derivatives have use in the prophylaxis and treatment of clinical conditions for which an inhibitor of NO synthase is indicated, in particular, an inhibitor of iNOS. Such conditions include inflammatory conditions, shock states, immune disorders, and disorders of gastrointestinal motility. The compounds of formula (I) and pharmaceutically acceptable salts,solvates, and physiologically functional derivatives thereof may also be of use in the prophylaxis and treatment of diseases of the central nervous system including migraine.

By shock states is meant those resulting from overproduction of NO, such as septic shock, haemorrhagic shock, traumatic shock, or shock caused by fulminant hepatic failure or by therapy with cytokines such as TNF, IL-1 and IL-2 or therapy with cytokine-inducing agents, for example 5,6-dimethylxanthenone acetic acid.

Examples of inflammatory conditions and immune disorders include those of the joint, particularly arthritis (e.g. rheumatoid arthritis, osteoarthritis, prosthetic joint failure), or the gastrointestinal tract (e.g. ulcerative colitis, Crohn's disease, and other inflammatory bowel diseases, gastritis and mucosal inflammation resulting from infection, the enteropathy provoked by non-steroidal antiinflammatory drugs), of the lung (e.g. adult respiratory distress syndrome, asthma, cystic fibrosis, or chronic obstructive pulmonary disease), of the heart (e.g. myocarditis), of nervous tissue (e.g. multiple sclerosis), of the pancreas (e.g. diabetes melitus and complications thereof), of the kidney (e.g. glomerulonephritis), of the skin (e.g. dermatitis, psoriasis, eczema, urticaria), of the eye (e.g. glaucoma) as well as of transplanted organs (e.g. rejection) and multi-organ diseases (e.g. systemic lupus erythematosis) and inflammatory sequelae of viral or bacterial infections. There is also evidence that iNOS inhibitors may be useful in the prophylaxis or treatment of bacterial infections (e.g. pneumonia), in particular, by reducing bacterial load in an infected mammal.

Furthermore, there is evidence for overproduction of NO by iNOS in atherosclerosis and following hypoxic or ischaemic insults (with or without reperfusion), for example in the brain or in ischaemic heart disease.

Disorders of gastrointestinal motility include ileus, for example post-operative ileus and ileus during sepsis.

By diseases of the central nervous system is meant those for which overproduction of NO is implicated, for example migraine, psychosis, anxiety, schizophrenia, sleep disorders, cerebral ischaemia, CNS trauma, epilepsy, multiple sclerosis, AIDS dementia, chronic neurodegenerative disease (e.g. Lewy Body Dementia, Huntington's disease, Parkinson's disease, or Alzheimer's disease) and acute and chronic pain, and conditions in which non-adrenergic non-cholinergic nerve may be implicated such as priapism, obesity and hyperphagia.

Examples of acute pain include musculoskeletal pain, post operative pain and surgical pain. Examples of chronic pain include chronic inflammatory pain (e.g. rheumatoid arthritis and osteoarthritis), neuropathic pain (e.g. post herpetic neuralgia, diabetic neuropathies associated with diabeties, trigeminal neuralgia, pain associated with functional bowel disorders, e.g. irritable bowel syndrome, non cardiac chest pain and sympathetically maintained pain) and pain associated with cancer and fibromyalgia.

Furthermore, inhibition of NO synthase may be of advantage in preventing the lymphocyte loss associated with HIV infection, in increasing the radiosensitivity of tumours during radiotherapy and in reducing tumour growth, tumour progression, angiogenesis, and metastasis.

Accordingly, the present invention provides a method for the prophylaxis or treatment of a clinical condition in a mammal, such as a human, for which an inhibitor of nitric oxide synthase, for example, an iNOS inhibitor is indicated, which comprises administration of a therapeutically effective amount of a compound of formula (I), or a pharmaceutically acceptable salt, solvate, or physiologically functional derivative thereof. In particular, the present invention provides a method for the prophylaxis or treatment of an inflammatory and/or immune disorder, such as arthritis or asthma. In a preferred aspect the present invention provides a method for the prophylaxis or treatment of a clinical condition selected from arthritis, asthma, ileus, and migraine. In a further aspect, the present invention provides a method for the prophylaxis or treatment of a bacterial infection.

In the alternative, there is also provided a compound of formula (I) or a pharmaceutically acceptable salt, solvate, or physiologically functional derivative thereof for use in medical therapy, particularly, for use in the prophylaxis or treatment of a clinical condition in a mammal, such as a human, for which an inhibitor of nitric oxide synthase, for example an iNOS inhibitor, is indicated. In particular, there is provided a compound of formula (I) or a pharmaceutically acceptable salt, solvate, or physiologically functional derivative thereof for the prophylaxis or treatment of an inflammatory and/or immune disorder, such as arthritis or asthma. In a preferred aspect, there is provided a compound of formula (I) or a pharmaceutically acceptable salt, solvate, or physiologically functional derivative thereof for the prophylaxis or treatment of arthritis, asthma, ileus, and migraine. In a further aspect, there is provided a compound of formula (I) or a pharmaceutically acceptable salt, solvate, or physiologically functional derivative thereof for the prophylaxis or treatment of a bacterial infection.

The amount of a compound of formula (I), or a pharmaceutically acceptable salt, solvate, or physiologically functional derivative thereof which is required to achieve a therapeutic effect will, of course, vary with the particular compound, the route of administration, the subject under treatment, and the particular disorder or disease being treated. The compounds of the invention may be administered orally or via injection at a dose of from 0.1 to 1500 mg/kg per day, preferably 0.1 to 500 mg/kg per day. The dose range for adult humans is generally from 5 mg to 35 g/day and preferably 5 mg to 2 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

While it is possible for the compound of formula (I), or a pharmaceutically acceptable salt, solvate, or physiologically functional derivative thereof to be administered alone, it is preferable to present it as a pharmaceutical formulation.

Accordingly, the present invention further provides a pharmaceutical formulation comprising a compound of formula (I) or a pharmaceutically acceptable salt, solvate, or physiologically functional derivative thereof, and a pharmaceutically acceptable carrier or excipient, and optionally one or more other therapeutic ingredients.

The present invention also provides the use of a compound of formula (I), or a pharmaceutically acceptable salt, solvate, or physiologically functional derivative thereof in the manufacture of a medicament for the prophylaxis or treatment of a clinical condition for which an inhibitor of nitric oxide synthase, for example an iNOS inhibitor, is indicated, for example an inflammatory and/or immune disorder, such as arthritis or asthma. In a preferred aspect, there is provided a compound of formula (I), or a pharmaceutically acceptable salt, solvate, or physiologically functional derivative thereof in the manufacture of a medicament for the prophylaxis or treatment of a clinical condition selected from arthritis, asthma, ileus, and migraine. In a further aspect, there is provided a compound of formula (I), or a pharmaceutically acceptable salt, solvate, or physiologically functional derivative thereof in the manufacture of a medicament for the prophylaxis or treatment of a bacterial infection.

Hereinafter, the term "active ingredient" means a compound of formula (I), or a pharmaceutically acceptable salt, solvate, or physiologically functional derivative thereof.

The formulations include those suitable for oral, parenteral (including subcutaneous, intradermal, intramuscular, intravenous and intraarticular), inhalation (including fine particle dusts or mists which may be generated by means of various types of metered dose pressurised aerosols, nebulisers or insufflators), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials. and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

According to a further aspect of the invention, there is provided a process for preparing a compound of formula (I) or a salt, solvate, or physiologically functional derivative thereof which comprises:

(i) reaction of the compound of formula (II)

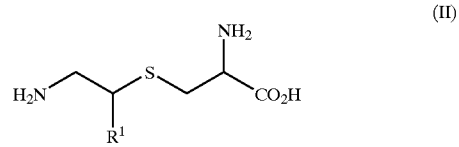

(II)

or an optical isomer, a salt, or a protected derivative thereof, wherein $R^1$ is as defined above, with a compound of formula (III)

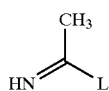 (III)

or a salt thereof, wherein L is a leaving group, most suitably a $C_{1-6}$ alkoxy group, for example ethoxy, or an alkylthio, aralkylthio or arylthio group e.g. a benzylthio, or 1- or 2-naphthylmethylthio group; followed by the following steps in any order:

(ii) optional removal of any protecting groups;

(iii) optional separation of an optical isomer from a mixture of optical isomers;

(iv) optional conversion of the product to a corresponding salt, solvate, or physiologically functional derivative thereof.

When L is $C_{1-6}$ alkoxy, the reaction in step (i) above may be effected in solution at alkaline pH, for example pH 8 to 11, suitably at pH 10.5, and at a low temperature, for example −5° C. to 20° C., suitably 0 to 5° C. When L is an alkylthio, aralkylthio, or arylthio group, the reaction may be effected in an organic solvent e.g. tetrahydrofuran or a $C_{1-4}$alcohol such as ethanol, at a moderate temperature e.g. 10 to 40° C., suitably at ambient temperature.

Compounds of formula (III) and salts thereof are available commercially or may be prepared by methods of organic chemistry well known to the person skilled in the art, for example, as described by Shearer et al in Tetrahedron Letters, 1997, 38, 179–182.

Compounds of formula (II) and salts and protected derivatives thereof may be prepared from a compound of formula (IV):

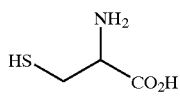 (IV)

or a protected derivative thereof, by coupling with a compound of formula (V)

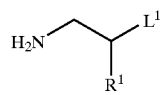 (V)

or a protected derivative thereof, wherein $R^1$ is as defined above and $L^1$ is a leaving group, for example halo, such as bromo, or an alkyl, aryl or aralkyl sulphonate ester, such as toluenesulphonyl.

Protected derivatives of a compound of formula (IV) e.g. N-t-butoxycarbonyl cysteine t-butyl ester may react with compounds of formula (V) under conditions in an appropriate organic solvent (e.g. toluene) in a reaction mediated by a base such as 1,8-diazabicyclo[5.4.0]undec-7-ene or a similar agent which would be recognised by one skilled in the art.

Alternatively, compounds of formula (II) and salts and protected derivatives thereof may be prepared by reduction (for example, using a metal hydride complex) of a compound of formula (VI)

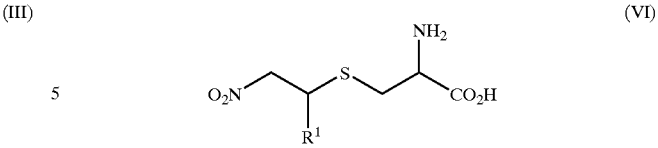 (VI)

or a protected derivative thereof, wherein $R^1$ is as defined above.

Compounds of formula (VI) may be prepared by methods analogous to those described by Yanagisawa et al in J. Med. Chem 30 (11), 1984–91, (1987) and Hassner and Dehaen in J. Org. Chem., 55, 5505–5510, (1990). Thus, reaction of the compound of the formula (IV) or a protected derivative thereof (for example, where the amino group is protected with an acyl group such as t-butoxycarbonyl and the carboxylic acid group is protected as an ester, such as a tert-butyl ester) with nitromethane and the appropriate aldehyde $R^1CHO$, wherein $R^1$ is as defined above, in the presence of piperidine yields a nitro compound of formula (VI) or a protected derivative thereof.

Compounds of formula (II) or a protected derivative thereof may also be prepared by reaction of a compound of formula (VII)

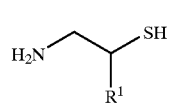 (VII)

or a protected derivative thereof wherein $R^1$ is as defined above, with an aziridine of formula (VIII).

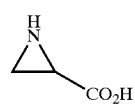 (VIII)

or a protected derivative thereof, for example, wherein the amine is protected with an acyl group such as t-butoxycarbonyl and the acid is protected as an ester such as $C_{1-4}$alkyl ester. The reaction of the compounds of formulae (VII) and (VIII) may be effected in an inert solvent, such as chloroform in the presence of a Lewis acid, such as $BF_3(OEt)_2$.

The compounds of formulae (IV), (V), (VII), and (VIII) and protected derivatives thereof are commercially available or may be prepared by methods of organic chemistry well known to the person skilled in the art.

The protecting groups used in the preparation of compounds of formula (I) may be used in a conventional manner, for example, using methods described in "Protective Groups in Organic Synthesis" by Theodora W Green, 2nd edition (John Wiley and Sons, 1991) which also describes methods for the removal of such groups.

In the above reactions, primary amines are suitably protected using acyl groups, such as t-butoxycarbonyl or benzyloxycarbonyl groups which may be removed under acidic conditions, for example, by treatment with hydrochloric acid or hydrobromic acid, or by hydrogenolysis.

As will be appreciated by the person skilled in the art use of such protecting groups may include orthogonal protection of amino groups in the compounds of formula (II) to facilitate the selective removal of one group in the presence of another, thus enabling selective functionalisation of a single amino function. For example, a benzyloxycarbonyl group may be selectively removed by hydrogenolysis. A person skilled in the art will also appreciate other orthogonal protection strategies, available by conventional means as described in Theodora W Green (vide supra).

The enantiomeric compounds of the invention may be obtained (a) by separation of the components of the corresponding racemic mixture, for example, by means of a chiral chromatography column, enzymatic resolution methods or preparing and separating suitable diastereoisomers, or (b) by direct synthesis from the appropriate chiral intermediates by the methods described above.

Optional conversion of a compound of formula (I) to a corresponding salt may conveniently be effected by reaction with the appropriate acid or base. Optional conversion of a compound of formula (I) to a corresponding solvate or physiologically functional derivative may be effected by methods known to those skilled in the art.

According to a further aspect, the present invention provides novel intermediates for the preparation of compounds of formula (I), for example: compounds of formula (II) as defined above, or an optical isomer, a salt, or a protected derivative thereof; particularly, a compound selected from:

(R,R)-t-butyl-2N-t-butoxycarbonyl-2,6-diamino-5-methyl-4-thiohexanoate;

(R,S)-t-butyl-2N-t-butoxycarbonyl-2,6-diamino-5-methyl-4-thiohexanoate;

(S,S)-t-butyl-2N-t-butoxycarbonyl-2,6-diamino-5-methyl-4-thiohexanoate;

(S,R)-t-butyl-2N-t-butoxycarbonyl-2,6-diamino-5-methyl-4-thiohexanoate;

(R,R/S)-t-butyl-2N-t-butoxycarbonl-2,6-diamino-5-ethyl-4-thiohexanoate;

(R,R/S)-t-butyl-2N-t-butoxycarbonyl-2,6-diamino-5-butoxymethyl-4-thiohexanoate;

(R,R/S)-t-butyl-2N-t-butoxycarbonyl-2,6-diamino-5-cyclopropyl-4-thiohexanoate;

(R,R)-t-butyl-2N-t-butoxycarbonyl-6N-benzyloxycarbonyl-2,6-diamino-5-methyl-4-thiohexanoate;

(R,S)-t-butyl-2N-t-butoxycarbonyl-6N-benzyloxycarbonyl-2,6-diamino-5-methyl-4-thiohexanoate;

(S,S)-t-butyl-2N-t-butoxycarbonyl-6N-benzyioxycarbonyl-2,6-diamino-5-methyl-4-thiohexanoate;

(S,R)-t-butyl-2N-t-butoxycarbonyl-6N-benzyloxycarbonyl-2,6-diamino-5-methyl-4-thiohexanoate;

(R,R/S)-t-butyl-2N-t-butoxycarbony-6N-benzyloxycarbonyl-2,6-diamino-5-ethyl-4-thiohexanoate; and (R,R/S)-t-butyl-2N-t-butoxycarbony-6N-benzytoxycarbonyl-2,6-diamino-5-butoxymethyl-4-thiohexanoate.

In a particular aspect of the invention, the compound of formula (II) is selected from (R,R)-t-butyl-2N-t-butoxycarbonyl-2,6-diamino-5-methyl-4-thiohexanoate and (R,R)-t-butyl-2N-t-butoxycarbonyl-6N-benzyloxycarbonyl-2,6-diamino-5-methyl-4-thiohexanoate.

Certain protected derivatives of the compounds of formula (VI) are also useful as intermediates for the preparation of compounds of formula (II); particularly (R,R/S)-t-butyl-2N-t-butoxycarbonyl-2-amino-5-cyclopropyl-6-nitro-4-thiohexanoate.

Certain protected derivatives of the compounds of formula (I) are also useful as intermediates for the preparation of compounds of formula (I); particularly a compound selected from:

(R,R)-t-butyl-2N-t-butoxycarbonyl-6N-(1-iminoethyl)-2,6-diamino-5-methyl-4-thiohexanoate;

(R,S)-t-butyl-2N-t-butoxycarbonyl-6N-(1-iminoethyl)-2,6-diamino-5-methyl-4-thiohexanoate;

(S,S)-t-butyl-2N-t-butoxycarbonyl-6N-(1-iminoethyl)-2,6-diamino-5-methyl-4-thiohexanoate;

(S,R)-t-butyl-2N-t-butoxycarbonyl-6N-(1-iminoethyl)-2,6-diamino-5-methyl-4-thiohexanoate;

(R,R/S)-t-butyl-2N-t-butoxycarbonyl-6N-(1-iminoethyl)-2,6-diamino-5-ethyl-4-thiohexanoate;

(R,R/S)-t-butyl-2N-t-butoxycarbonyl-6N-(1-iminoethyl)-2,6-diamino-5-butoxymethyl-4-thiohexanoate; and (R,R/S)-t-butyl-2N-t-butoxycarbonyl-6N-(1-iminoethyl)-2,6-diamino-5-cyclopropyl-4-thiohexanoate;

and salts and solvates thereof.

In a particular aspect of the invention, the protected derivative of formula (I) is (R,R)-t-butyl-2N-t-butoxycarbonyl-6N-(1-iminoethyl)-2,6-diamino-5-methyl-4-thiohexanoate or a salt or solvate thereof.

For a better understanding of the invention, the following Examples are given by way of illustration.

SYNTHETIC EXAMPLES

Example 1

Synthesis of (R,R)-6N-(1-Iminoethyl)-2,6-diamino-5-methyl-4-thiohexanoate Dihydrochloride or S-[(R)-2-(1-Iminoethylamino)propyl]-L-cysteine Dihydrochloride (a) (R,R)-t-Butyl-2N-t-butoxycarbonyl-6N-benzyloxycarbonyl-2,6-diamino-5-methyl-4-thiohexanoate To a solution of N-t-butoxycarbonyl cysteine t-butyl ester (7.26 g, 26.2 mmol) (Olsen et al., J Med. Chem., 1985, 50(22), 4332–4336) in dry toluene (100 ml) was added (S)-N-benzyloxycarbonyl 1-aminopropan-2-ol tosylate (9.51 g, 26.2 mmol) and 1,8-diazabicyclo[5.4.0]undec-7-ene (3.90 ml, 26.2 mmol) and the mixture stirred vigorously overnight at 60° C. under nitrogen. The mixture was partitioned between 250 ml each of ethyl acetate and 1N aqueous HCl. A further organic extract was combined and these extracts were washed with aqueous sodium bicarbonate, water and brine, then dried and evaporated. Purification by column chromatography afforded the title compound as a colourless oil which crystallised to give a white solid on prolonged standing.

LC/Electrospray Mass Spec., RT 4.93 min, M+H 469 (100%), M+NH$_4^+$ 486 (70%); $^1$H NMR (CDCl$_3$) $\delta_H$; 1.27 (3H, d, Me), 1.44 and 1.47 (ea 9H, s, CMe$_3$), 2.92 (3H, m, 3-H, 5-H), 3.23 and 3.38 (ea 1H, m, 6-H), 4.39 (1H, brm, 2-H), 5.11 (2H, s, CH$_2$Ph) 5.31 and 5.42 (ea 1H, br, NH), 7.34 (5H, m, Ar-H). Circular Dichroism spectrum (MeCN) 210 (+0.42) and 233 (−0.11) nm.

(b) (R,R)-t-Butyl-2N-t-butoxycarbonyl-2,6-diamino-5-methyl-4-thiohexanoate

To a solution of (R,R)-t-butyl-2N-t-butoxycarbonyl-6N-benzyloxycarbonyl-2,6-diamino-5-methyl-4-thiohexanoate (5 g) in 120 ml of Ethanol, degassed and blanketed with nitrogen, was added 2.5 g of Palladium hydroxide on charcoal (20%, Degussa type E101 NE/W, 1:1 with water) followed by ammonium formate (10 g). The solution was then heated and refluxed for 1 hour, after which it was cooled and filtered through hyflo, well-washed with aqueous ethanol. This was evaporated and the residue passed down a short silica column eluted with 90:10:0.5 chloroform: methanol: 880 ammonia, to yield an oil on evaporation which was taken directly to the next stage.

LC/Electrospray Mass Spec., RT 2.40 minutes, M+H 335 (100%), 279 (60%)

(c) (R,R)-t-Butyl-2N-t-butoxycarbonyl-6N-(1-iminoethyl)- 2,6-diamino-5-methyl-4-thiohexanoate Hydrochloride.

A single portion of S-(1-naphthylmethyl)thioacetimidate hydrochloride (3.10 g, 12.3 mmol) was added to a solution of (R,R)-t-butyl-2N-t-butoxycarbonyl-6N-2,6-diamino-5-methyl-4-thiohexanoate 2.75 g in 50 ml of ethanol under nitrogen and the solution stirred for 14 h at room temperature. The solvent was evaporated and the residue partitioned between 50 ml each of ether and water, followed by 2 ether washes; back aqueous extracts were combined and evaporated to give a crude white amorphous paste which was used directly in the next stage.

Thermospray Mass spectrum M+H 376 (100%), 276 (12%). $^1$H NMR (D$_2$O) $\delta_H$; 1.28 (3H, d, Me), 1.39 and 1.42 (ea 9H, s, CMe$_3$), 2.21 (3H, s, CH$_3$) 3.01 (3H, m, 3-H, 5-H), 3.37 (2H, m, 6-H), 4.18 (1H, t, 2-H).

(d) (R,R)-6N-(1-Iminoethyl)-2,6-diamino-5-methyl-4-thiohexanoate Dihydrochloride; or S-[(R)-2-(1-Iminoethylamino)propyl]-L-cysteine Dihydrochloride.

(R,R)-t-butyl-2N-t-butoxycarbonyl-6N-(1-iminoethyl)-2, 6-diamino-5-methyl-4-thiohexanoate hydrochloride was dissolved by the addition of 20 ml of 4N hydrogen chloride in dioxane and the soon-formed suspension vigorously stirred overnight under nitrogen. 50 ml of ether was added and the liquid was decanted form the sticky gum. Trituration with ether ultimately afforded the title compound as an amorphous hygroscopic white solid.

Electrospray Mass spectrum M+H 220 (100%), $^1$H NMR (D$_2$O) $\delta_H$; 1.37 (3H, d, Me), 2.25 (3H, s, CH$_3$) 3.23 (3H, m, 3-H, 5-H), 3.47 (2H, m, 6-H), 4.24 (1H, t, 2-H) (note that there is some doubling of signals due to rotameric forms). $^{13}$C NMR (DMSO-d$_6$) $\delta_C$; 18.90 (q, Me), 19.30 (q, Me), 30.13 (t, 3-C), 38.83 (d, 5-C), 47.43 (t, 6-C) 52.20 (d, 2-C), 165.0 (s, N=C—N), 170.0 (s, CO$_2$H). Circular Dichroism spectrum (H$_2$O) 199 (+1.38) and 223 (−0.77) nm.

Example 2

Synthesis of (R,S)-6N-(1-Iminoethyl)-2,6-diamino-5-methyl-4-thiohexanoate Dihydrochloride or S-[(S)-2-(1-Iminoethylamino)propyl]-L-cysteine Dihydrochloride The procedures and methods were identical to those used in Example 1, except that in the alkylation step, protected L-Cysteine was reacted with (R)-N-benzyloxycarbonyl 1-aminopropan-2-ol tosylate instead of the (S)-enantiomer of that example.

Electrospray Mass spectrum M+H 220 (100%), $^1$H NMR (D$_2$O) $\delta_H$; 1.40 (3H, d, Me), 2.25 (3H, s, CH$_3$) 3.30 (3H, m, 3H, 5-H), 3.45 (2H, m, 6-H), 4.25 (1H, t, 2-H) (n.b. some doubling of signals due to rotameric forms).

Example 3

Synthesis of (S,S)-6N-(1-Iminoethyl)-2,6-diamino-5-methy-4-thiohexanoate Dihydrochloride or S-[(S)-2-(1-Iminoethylamino)propyl]-D-cysteine Dihydrochloride The procedures and methods were identical to those used in Example 1, except that in the alkylation step, the enantiomeric protected D-Cysteine was reacted with (R)-N-benzyloxycarbonyl 1-aminopropan-2-ol tosylate.

Product spectra identical to those of compound in Example 1, except: Circular Dichroism spectrum (H$_2$O) 199 (−1.05) and 224 (+0.66) nm.

Example 4

Synthesis of (S,R)-6N-(1-Iminoethyl)-2,6-diamino-5-methyl-4-thiohexanoate Dihydrochloride or S-[(R)-2-(1-Iminoethylamino)propyl]-D-cysteine Dihydrochloride The procedures and methods were identical to those used in Example 1, except that in the alkylation step, the enantiomeric protected D-Cysteine was reacted with (R/S)-N-benzyloxycarbonyl 1-aminopropan-2-ol tosylate.

Electrospray Mass spectrum M+H 220 (100%), $^1$H NMR (D$_2$O) $\delta_H$; 1.40 (3H, d, Me), 2.25 (3H, s, CH$_3$) 3.30 (3H, m, 3-H, 5-H), 3.45 (2H, m, 6-H), 4.25 (1H, t, 2-H).

Example 5

Synthesis of (R,R/S)-6N-(1-Iminoethyl)-2,6-diamino-5-ethyl-4-thiohexanoate Dihydrochloride or S-[(R/S)-2-(1-Iminoethylamino)butyl]-L-cysteine Dihydrochloride The procedures and methods were identical to those used in Example 1, except that in the alkylation step, protected L-Cysteine was reacted with (R/S)-N-benzyloxycarbonyl 1-aminobutan-2-ol tosylate instead of the 1-aminopropan-2-ol derivative of that example, to furnish a product that was substantially an epimeric mixture of the title compound.

Electrospray Mass spectrum M+H 234 (100%).

Example 6

Synthesis of (R,R/S)-6N-(1-Iminoethyl)-2,6-diamino-5-hydroxymethyl-4-thiohexanoate Dihydrochloride or S-[(R/S)-2-(1-Iminoethylamino, 3-hydroxy)propyl]-L-cysteine Dihydrochloride The procedures and methods were identical to those used in Example 1, except that in the alkylation step, protected L-Cysteine was reacted with (R/S)-N-benzyloxycarbonyl-3-t-butoxy-1-aminopropan-2-ol tosylate instead of the 1-aminopropan-2-ol derivative of that example. This furnished a product that was substantially an epimeric mixture of the title compound with concomitant loss of the tert butyl ether in the deprotection stage.

Electrospray Mass spectrum M+H 236 (100%).

Example 7

Synthesis of S-[(R/S)-2-(1-Iminoethylamino, 2-Cyclopropyl)ethyl]-L-cysteine Dihydrochloride or S-[(R/S)-2-(1-Iminoethylamino, 2-Cyclopropyl) ethyl]-L-cysteine Dihydrochloride a) (R,R/S)-t-Butyl-2N-t-butoxycarbonyl-2-amino-5-cyclopropyl-6-nitro-4-thiohexanoate Protected L-Cysteine was reacted with nitromethane, piperidine and cyclopropanecarboxaldehyde using the conditions described by Hassner and Dehaen in J. Org. Chem., 55, 5505–5510, (1990), affording the title compound as a colourless oil.

$^1$H NMR (CDCl$_3$) $\delta_H$; 0.40 and 0.68 (ea 2H, m, cyclopropyl-H), 0.89 (1H, m, cyclopropyl-H), 1.46 and 1.48 (ea 9H, s, CMe$_3$), 2.81, 3.00 and 3.10 (ea 1H, m, 3-H, 5-H), 4.41 (1H, brm, 2-H), 4.58 (2H, m, 6-H), 5.34 (1H, br, NH).

b) (R,R/S)-t-Butyl-2N-t-butoxycarbonyl-2,6-diamino-5-cyclopropyl-4-thiohexanoate The nitro groups of the intermediate from step a) was reduced using a mixture Nickel Chloride/Sodium Borohydride in methanol according to the method described by Nagarajan and Ganem, J. Org. Chem., 51, 4856–4861, (1990). An oil was recovered after silica gel solid phase extraction, which was used directly in the next stage.

c) Synthesis of (R,R/S)-t-Butyl-2N-t-butoxycarbonyl-6N-(1-iminoethyl)-2,6-diamino-5-cyclopropyl-4-thiohexanoate The product from the reduction step b) (47 mg, 0.13 mmol) above was reacted with S-(1-naphthylmethyl)thioacetimidate hydrochloride (72 mg) as described in step c) of Example 1 to yield a crude white foam.

$^1$H NMR (D$_2$O) $\delta_H$; 0.05 and 0.34 (ea 2H, m, cyclopropyl-H), 0.59 (1H, m, cyclopropyl-H), 1.09 and 1.12 (ea 9H, s, CMe$_3$), 1.92 (3H, s Me), 2.05 (1H, m, 5-H), 2.70 (2H, m, 3-H), 3.25, (2H, m, 6-H) 3.89 (1H, m, 2-H). Electrospray Mass spectrum M+H 402 (50%), d) Synthesis of S-[(R,S)-2-(1-Iminoethylamino, 2-Cyclopropyl)ethyl]-L-cysteine Dihydrochloride or S-[(R/S)-2-(1-Iminoethylamino, 2-Cyclopropyl)ethyl]-L-cysteine Dihydrochloride The deprotection of (R,R/S)-t-butyl-2N-t-butoxycarbonyl-6N-(1-iminoethyl)-2,6-diamino-5-cyclopropyl-4-thiohexanoate was carried out using 4N HCl in dioxane. The product, a mixture of epimers at C-5, was isolated as a hygroscopic glassy solid after a C-18 solid phase extraction eluted with water.

$^1$H NMR (D$_2$O) $\delta_H$; 0.29 and 0.58 (ea 2H, m, cyclopropyl-H), 0.82 (1H, m, cyclopropyl-H), 2.14 (3H, s Me), 2.34 (1H, m, 5-H), 3.12 (2H, m, 3-H), 3.48, (2H, m, 6-H) 3.98 (1H, m, 2-H). Electrospray Mass spectrum M+H 246 (100%).

BIOLOGICAL ACTIVITY

1. Inhibition of Isolated Human iNOS

The inhibition of purified human iNOS may be determined using a preparation of human iNOS as described in the chapter "Expression if Human Nitric Oxide Synthase Isozymes" by Charles et al in Methods in Enzymology, 1996 Volume 268, 449–460. Activity may be monitored using quantitative absorption changes of haemoglobin as described by R. G. Knowles and J. Dawson in "A Microtitreplate Assay of Human NOS Isoforms" in Methods in Molecular Biology, 1998, Volume 100, 237–242, Nitric Oxide Protocols, Ed M. A. Titheradge, Humana Press, Totowa N.J.

| Compound | IC50 ($\mu$M) |
|---|---|
| Example 1 | 2.0 |
| Example 2 | 39.0 |
| Example 3 | 6.6 |
| Example 4 | 48.0 |
| Example 7 | 6.2 |

2. Inhibition of eNOS and INOS in Rat Aortic Rings

The inhibition of eNOS and iNOS in situ in rat aortic rings was assessed by measuring the increases in ring tension caused by NO synthase inhibition. For studies of basal tone (reflecting eNOS), rings of thoracic aorta with intact endothelium were prepared as described previously (Rees et at. (1989) Br. J. Pharmol. 96, 418–424) and cumulative concentration curves obtained for the inhibitors in the presence of a threshold concentration of phenylephrine (ED$_{10}$≈10 nM). For studies of induced smooth muscle tone (reflecting iNOS), endothelium-denuded rings were exposed to LPS (0.1 $\mu$g/ml from S. typhosa) in the presence of phenylephrine at approximately ED$_{90}$ for 6 h as described previously (Rees et al. (1990) Biochem. Biophys. Res. Commun. 173, 541–547). During this time a progressive loss of tone occurred because of iNOS induction. Cumulative concentration curves were then obtained for the inhibitors.

The results are given in the following table:

|  | iNOS IC$_{50}$($\mu$M) | eNOS IC$_{50}$ ($\mu$M) | selectivity iNOS vs eNOS |
|---|---|---|---|
| Example 1 | 0.26 | >20 | >75 |

3. Inhibition of nNOS in Rat Cortical Slices

The effects of compounds on nNOS in rat brain slices was determined as described in Furfine et al (1994) J. Biol. Chem. 269, 26677–26683 and Lizasoain et al (1995) J. Neurochem. 64, 636–642. KCl (54 mM)—stimulated NO synthesis was measured by the conversion of 14C-arginine to 14C-citrulline over a 2 h period at 37° C. in Mcllwain—chopped (0.2 mm x0.2 mm) rat cerebral cortex slices, following a 1 h preincubation period in the absence of compound or high KCl.

The compound of Example 1 was determined to have an IC$_{50}$ of >80 $\mu$M, suggesting approximately >300-fold selectivity for iNOS versus nNOS.

4. Method for Determining the Oral Bioavailability of iNOS Inhibitor Compounds

Animal Work:

Rats (3 animals per time point) were dosed intravenously (10 mg/kg) and orally (50 mg/kg) with test compound in an aqueous solution. Blood samples were taken at time intervals after administration and plasma prepared by centrifugation. Samples were stored at −20° C. until analysis.

Analysis of Compounds in Plasma:

Plasma (50 $\mu$l) was de-proteinated and compound derivatised with a quaternary ammonium reagent. Samples were then injected onto an HPLC system and compound concentration determined using mass spectrometric detection.

Pharmacokinetic Analysis:

The plasma concentrations obtained by the above method were entered into a pharmacokinetic software package (PKCAL v 1.2s) and the data were fitted using a non-compartmental method. The oral bioavailability of the compounds was determined by comparing the Area Under the Curve (AUC) values calculated by the software for the oral profile with the AUC for the intravenous profile. The half-lives were obtained by fitting the terminal phase time points of the intravenous profile.

The compound of example 1 was found to have an oral bioavailability of >90% and a half-life of 2–4 hours.

What is claimed is:

1. A method for the prophylaxis or treatment of neuropathic pain in a mammal, said method comprising administering to said mammal a therapeutically effective amount of a compound of formula (I):

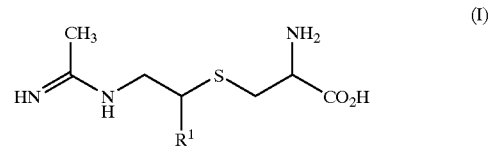

or a pharmaceutically acceptable salt, solvate, or physiologically functional derivative thereof;

wherein $R^1$ is selected from the group consisting of $C_{1-4}$ alkyl, $C_{3-4}$ cycloalkyl, $C_{1-4}$ hydroxyalkyl, and $C_{1-4}$ haloalkyl.

2. The method according to claim 1, wherein said mammal is a human.

3. The method according to claim 1, wherein said compound of formula (I) is selected from the group consisting of:
   S-((R)-2-(1-iminoethylamino)propyl)-L-cysteine;
   S-((S)-2-(1-iminoethylamino)propyl)-L-cysteine;
   S-((R/S)-2-(1-iminoethylamino)propyl)-L-cysteine;
   S-((R)-2-(1-iminoethylamino)propyl)-D-cysteine;
   S-((S)-2-(1-iminoethylamino)propyl)-D-cysteine;
   S-((R/S)-2-(1-iminoethylamino)propyl)-D-cysteine;
   S-((R/S)-2-(1-iminoethylamino)butyl)-L-cysteine;
   S-((R/S)-2-(1-iminoethylamino,2-cyclopropyl)ethyl)-L-cysteine; and
   S-((R/S)-2-(1-iminoethylamino,3-hydroxy)propyl)-L-cysteine,
or a pharmaceutically acceptable salt, solvate, or physiologically functional derivative thereof.

4. The method according to claim 1, wherein said compound of formula (I) is S-((R)-2-(1-iminoethylamino)propyl)-L-cysteine or a pharmaceutically acceptable salt, solvate, or physiologically functional derivative thereof.

5. A method for the prophylaxis or treatment of irritable bowel syndrome in a mammal, said method comprising administering to said mammal a therapeutically effective amount of a compound of formula (I):

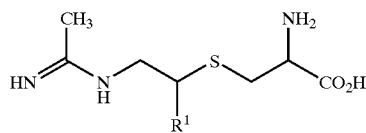

(I)

or a pharmaceutically acceptable salt, solvate, or physiologically functional derivative thereof;
   wherein $R^1$ is selected from the group consisting of $C_{1-4}$ alkyl, $C_{3-4}$ cycloalkyl, $C_{1-4}$ hydroxyalkyl, and $C_{1-4}$ haloalkyl.

6. The method according to claim 5, wherein said mammal is a human.

7. The method according to claim 5, wherein said compound of formula (I) is selected from the group consisting of:
   S-((R)-2-(1-iminoethylamino)propyl)-L-cysteine;
   S-((S)-2-(1-iminoethylamino)propyl)-L-cysteine;
   S-((R/S)-2-(1-iminoethylamino)propyl)-L-cysteine;
   S-((R)-2-(1-iminoethylamino)propyl)-D-cysteine;
   S-((S)-2-(1-iminoethylamino)propyl)-D-cysteine;
   S-((R/S)-2-(1-iminoethylamino)propyl)-D-cysteine;
   S-((R/S)-2-(1-iminoethylamino)butyl)-L-cysteine;
   S-((R/S)-2-(1-iminoethylamino,2-cyclopropyl)ethyl)-L-cysteine; and
   S-((R/S)-2-(1-iminoethylamino,3-hydroxy)propyl)-L-cysteine,
or a pharmaceutically acceptable salt, solvate, or physiologically functional derivative thereof.

8. The method according to claim 5, wherein said compound of formula (I) is S-((R)-2-(1-iminoethylamino)propyl)-L-cysteine or a pharmaceutically acceptable salt, solvate, or physiologically functional derivative thereof.

9. A method for the prophylaxis or treatment of chronic obstructive pulmonary disease in a mammal, said method comprising administering to said mammal a therapeutically effective amount of a compound of formula (I):

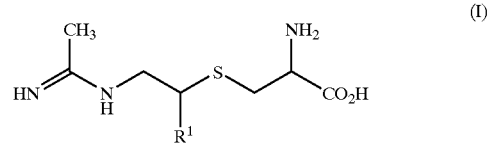

(I)

or a pharmaceutically acceptable salt, solvate, or physiologically functional derivative thereof;
   wherein $R^1$ is selected from the group consisting of $C_{1-4}$ alkyl, $C_{3-4}$ cycloalkyl, $C_{1-4}$ hydroxyalkyl, and $C_{1-4}$ haloalkyl.

10. The method according to claim 9, wherein said mammal is a human.

11. The method according to claim 9, wherein said compound of formula (I) is selected from the group consisting of:
   S-((R)-2-(1-iminoethylamino)propyl)-L-cysteine
   S-((S)-2-(1-iminoethylamino)propyl)-L-cysteine;
   S-((R/S)-2-(1-iminoethylamino)propyl)-L-cysteine;
   S-((R)-2-(1-iminoethylamino)propyl)-D-cysteine;
   S-((S)-2-(1-iminoethylamino)propyl)-D-cysteine;
   S-((R/S)-2-(1-iminoethylamino)propyl)-D-cysteine;
   S-((R/S)-2-(1-iminoethylamino)butyl)-L-cysteine;
   S-((R/S)-2-(1-iminoethylamino,2-cyclopropyl)ethyl)-L-cysteine; and
   S-((R/S)-2-(1-iminoethylamino,3-hydroxy)propyl)-L-cysteine,
or a pharmaceutically acceptable salt, solvate, or physiologically functional derivative thereof.

12. The method according to claim 9, wherein said compound of formula (I) is S-((R)-2-(1-iminoethylamino)propyl)-L-cysteine or a pharmaceutically acceptable salt, solvate, or physiologically functional derivative thereof.

* * * * *